(12) United States Patent
Bittenson

(10) Patent No.: US 8,043,308 B2
(45) Date of Patent: Oct. 25, 2011

(54) BONE SUTURE

(75) Inventor: Steven N. Bittenson, Bedford, MA (US)

(73) Assignee: DePuy Mitek, Inc., Raynham, MA (US)

( * ) Notice: Subject to any disclaimer, the term of this patent is extended or adjusted under 35 U.S.C. 154(b) by 752 days.

(21) Appl. No.: 11/611,094

(22) Filed: Dec. 14, 2006

(65) Prior Publication Data
US 2008/0147094 A1   Jun. 19, 2008

(51) Int. Cl.
*A61B 17/04* (2006.01)

(52) U.S. Cl. .................................................. 606/144

(58) Field of Classification Search .............. 606/144
See application file for complete search history.

(56) References Cited

U.S. PATENT DOCUMENTS

| | | | |
|---|---|---|---|
| 1,583,271 A * | 5/1926 | Biro | 606/144 |
| 4,263,913 A * | 4/1981 | Malmin | 606/187 |
| 4,743,632 A | 5/1988 | Marinovic | |
| 5,242,449 A * | 9/1993 | Zaleski | 606/107 |
| 5,250,055 A | 10/1993 | Moore | |
| 5,527,342 A * | 6/1996 | Pietrzak et al. | 606/232 |
| 5,637,112 A | 6/1997 | Moore et al. | |
| 5,665,110 A * | 9/1997 | Chervitz et al. | 606/232 |
| 5,681,333 A | 10/1997 | Burkhart et al. | |
| 5,722,981 A * | 3/1998 | Stevens | 606/148 |
| 5,782,845 A * | 7/1998 | Shewchuk | 606/144 |
| RE36,020 E * | 12/1998 | Moore et al. | 606/144 |
| 5,961,530 A * | 10/1999 | Moore et al. | 606/148 |
| 6,140,452 A | 10/2000 | Felt | |
| 6,306,177 B1 | 10/2001 | Felt | |
| 6,328,744 B1 | 12/2001 | Harari et al. | |
| 6,498,421 B1 | 12/2002 | Oh et al. | |
| 6,551,329 B1 | 4/2003 | Kortenbach et al. | |
| 6,620,185 B1 * | 9/2003 | Harvie et al. | 606/232 |
| 6,689,087 B2 | 2/2004 | Pal et al. | |
| 6,843,796 B2 | 1/2005 | Harari et al. | |

(Continued)

FOREIGN PATENT DOCUMENTS

EP   1607046 A1   12/2005

(Continued)

OTHER PUBLICATIONS

Bar-Cohen, Dr. Yoseph , "NASA Develops Drill for the Future" *Innovation Aerospace Technology*, vol. 8, No. 4, Jul./Aug. 2000, pp. 1-3 (Available at http://ipp.nasa.gov/innovation/Innovation_84/sbirnasa.html).

(Continued)

*Primary Examiner* — Darwin Erezo
*Assistant Examiner* — Son Dang

(57) ABSTRACT

Devices and methods useful for suturing soft tissue to bone are disclosed. In one embodiment, a bone-suturing device is provided and can include a delivery needle, a delivery needle driving element, a capture needle, and a capture needle driving element. The delivery needle driving element and capture needle driving element can advance the delivery needle and the capture needle through soft tissue and into bone, respectively, and the paths of the delivery needle and the capture needle can intersect therein. The delivery needle can be adapted for holding a suture and the capture needle can be adapted for receiving the suture held by the delivery needle. In another embodiment, an injection device can be provided to deliver an adhesive material into bone. The devices and methods disclosed herein can provide simple and minimally invasive ways to suture soft tissue to bone with a high resistance to pullout and reduced recovery time, and may be used as part of percutaneous, arthroscopic, or open surgical procedures.

11 Claims, 6 Drawing Sheets

U.S. PATENT DOCUMENTS

| | | |
|---|---|---|
| 6,863,136 B2 | 3/2005 | Bar-Cohen et al. |
| 2002/0040227 A1 | 4/2002 | Harari et al. |
| 2002/0165470 A1 | 11/2002 | Pal et al. |
| 2002/0193798 A1 | 12/2002 | Oh et al. |
| 2004/0049194 A1 | 3/2004 | Harvie |
| 2005/0043746 A1 | 2/2005 | Pollak et al. |
| 2005/0283170 A1 | 12/2005 | Battles et al. |
| 2006/0241657 A1 | 10/2006 | Cerundolo |

FOREIGN PATENT DOCUMENTS

| | | |
|---|---|---|
| JP | 2001079013 A | 3/2001 |

OTHER PUBLICATIONS

European Search Report for application No. 07254838.1 dated Apr. 15, 2010.

* cited by examiner

BONE SUTURE

FIELD OF THE INVENTION

The present invention relates to devices and methods for suturing soft tissue to bone.

BACKGROUND OF THE INVENTION

Many surgical procedures involve the attachment of soft tissue to bone. For example, to repair a torn rotator cuff, a surgeon may have to reattach a rotator cuff tendon to the humerus bone. A surgeon can stitch the tendon to the humerus by passing a suture through the tendon, anchoring the suture to the bone underneath, and securing the suture with a knot, fastener, or the like. Depending on the application, the suturing process may involve single-row, dual-row, or mattress stitching.

A number of approaches exist for suturing soft tissue to bone and particularly for the anchoring of a suture in bone. Some involve the use of suture anchors that are placed into holes drilled in the bone. A variety of suture anchors are available, including screw-type, toggle-type, barb-type, sprung tines, deployable or deformable arms, and knotless and/or expanding mechanisms. Other techniques involve passing a suture through a tunnel formed in the bone or manually pushing a suture into one hole formed in the bone and out of another, leaving two free ends of suture which can be secured above the soft tissue. More recent approaches involve the use of adhesives and/or reinforcing patches for the suture in conjunction with bone anchors or holes pre-drilled into the bone surface.

The need to pre-drill and/or substantially stress the bone surface is a significant drawback to many of these techniques. They also often result in considerable trauma to the overlying soft tissue, particularly where the footprint or exposed area of the bone must be relatively large. They can be difficult or impossible to perform percutaneously. In addition, the use of bone anchors leaves a foreign object in the body, which can be the cause of later complications.

There is a need in this art for novel devices and methods for attaching a suture to bone that exhibit high pull-out resistance, can be performed with low trauma to bone and overlying tissue, and that can be used percutaneously as well as arthroscopically and in open surgery.

SUMMARY OF THE INVENTION

Devices and methods useful for suturing soft tissue to bone are disclosed. In one exemplary embodiment, the device can include a delivery needle having an elongate body with a lumen defined therein, a proximal end, and a distal end with a piercing tip. The delivery needle can be adapted to hold a suture, for example in the lumen, in a second lumen adapted for holding the suture, or in a groove. A delivery needle driving element can be associated with the delivery needle, the delivery needle driving element being effective to distally advance the delivery needle into bone. In another embodiment, the delivery needle driving element can include a first ultrasonic driver. The device can further include a capture needle having an elongate body, a proximal end, and a distal end with a piercing tip. The capture needle can be disposed adjacent the delivery needle and adapted to receive the suture held by the delivery needle. In another embodiment, the capture needle and/or the delivery needle are optionally curved. A capture needle driving element can be associated with the capture needle, the capture needle driving element being effective to distally advance the capture needle into bone such that a path of the capture needle intersects a path of the delivery needle when the delivery needle is distally advanced, which intersection may occur in cancellous bone in some applications. The capture needle driving element can include a second ultrasonic driver. The device can also have one ultrasonic driver, with the delivery needle driving element including the ultrasonic driver and a coupling to the delivery needle and the capture needle driving element including the ultrasonic driver and a second coupling to the capture needle.

In another embodiment, a bone-suturing device can include a delivery needle having an elongate body with a lumen defined therein, a proximal end, and a distal end with a piercing tip and a capture needle having an elongate body, a proximal end, and a distal end with a piercing tip, the capture needle being disposed adjacent the delivery needle. The delivery needle and the capture needle can be arranged such that their paths intersect when both are distally advanced. The device can further include an ultrasonic driving element that is associated with the delivery needle for distally advancing the delivery needle into bone and that is associated with the capture needle for distally advancing the capture needle into bone. In other aspects, the device can include an injection device that is associated with the lumen of the delivery needle and that is effective to deliver an adhesive material therethrough to the distal end of the delivery needle.

Methods for suturing soft tissue to bone are also provided. In one exemplary embodiment, a method can include driving a delivery needle into bone, the delivery needle being adapted to deliver a suture to bone. The method can further include driving a capture needle into bone such that a path of the capture needle intersects a path of the delivery needle. The intersection can occur, for example, in cancellous bone. Either of the driving needle or capture needle can be driven first, or both needles can be driven together or in alternating stages. Driving the delivery needle and the capture needle can involve piercing soft tissue, and can be performed at least in part ultrasonically. A suture can be passed from the delivery needle to the capture needle to withdraw the suture through the path of the capture needle. At the intersection of the paths of the delivery needle and the capture needle an adhesive material can be delivered. The adhesive material can be delivered in part by ultrasonic energy. In yet other aspects, the method can include securing soft tissue to bone, for example by securing free ends of the suture outside the bone with a knot or fastener, or by placing the soft tissue on bone and driving the delivery needle and capture needle through the soft tissue to be sutured. In another embodiment, the method can be conducted percutaneously, and/or by inserting a cannula into the skin and inserting the delivery needle and the capture needle through the cannula.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides devices and methods for suturing soft tissue to bone. The devices and methods can be applied to suture soft tissue to bone in a wide range of applications, including suturing soft tissue to bone in percutaneous, arthroscopic, or open surgical procedures and also can be used for attaching sutures to bone itself, without soft tissue. Certain embodiments are described below in the context of suturing the rotator cuff tendon to the humerus, however these descriptions are by way of example only. The devices and methods disclosed herein can be used to implement and improve a variety of current surgical techniques, although those skilled in the art will no doubt find many applications for them, including their use in newly developed techniques.

Figure 1A:
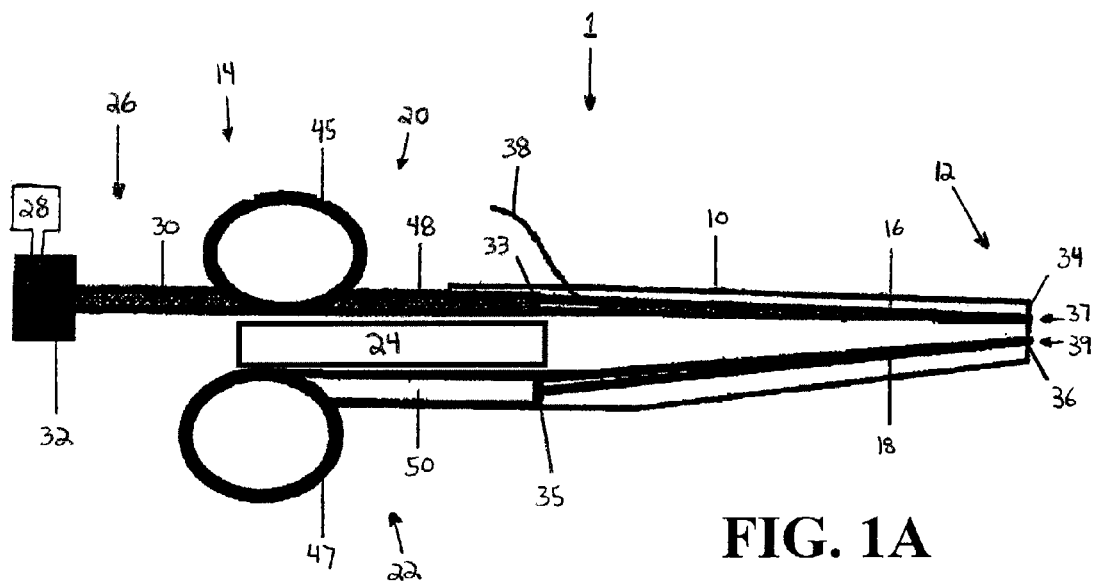
FIG. 1A illustrates one exemplary embodiment of a bone suturing device.

FIG. 1A illustrates one exemplary embodiment of a device 1 for suturing soft tissue to bone. The device 1 generally can include a body 10 with an operative distal end 12 and a proximal end 14. The device 1 can have a delivery needle 16 adapted to carry a suture 38 and a capture needle 18 adapted to capture or receive a suture 38 from the delivery needle 16. The delivery needle 16 can have the suture 38 disposed at its proximal end and threaded therethrough for delivery to the distal tip 34 of the delivery needle 16 where the suture 38 can be passed from the delivery needle 16 to the capture needle 18 while positioned within the bone, as discussed below. The delivery needle 16 can be associated with a delivery needle driving element 20 that is effective to advance the delivery needle 16 distally into a bone. Likewise, the capture needle 18 can be associated with a capture needle driving element 22 that is effective to advance the delivery needle 16 distally into a bone such that the path of the capture needle 18 intersects with a path of or tunnel formed by a distally advanced delivery needle 16. The device 1 can also have an optional ultrasonic driver 24 to supply a driving or excitatory force to advance, or aid in advancing, either or both of the delivery needle 16 or the capture needle 18 into bone. An injection device 26 can be arranged at the proximal end 33 of the delivery needle 16 to deliver an adhesive material 32, such as a bone cement, into the bone and can have a reservoir 28 to store or prepare the adhesive material 32 and an injection pump 30 to cause the adhesive material 32 to flow into the bone. The injection pump 30 can be effective to cause the adhesive material 32 to flow through the delivery needle 16 to the distal tip 34 thereof or, alternatively, through the capture needle 18 to the distal tip 36 thereof, or through both the delivery needle 16 and the capture needle 18.

The body 10 of the device 1 can have a wide variety of configurations. In the illustrated embodiment of FIG. 1A the body 10 of the device 1 is in the form of an elongate housing with a distal end 12 and proximal end 14. The body 10 can also be an elongate shaft or tube, cubic, rectangular, oval, bullet-shaped, or virtually any other shape and size. The body 10 can also be an arrangement or network of one or more connecting members, such as a shaft connecting the components of the device 1. The body 10 can have a pistol grip or scissors grip attached thereto, such as with a handheld medical instrument, which can be advantageous for use in an open surgery, arthroscopic procedures or percutaneous surgical procedures. Alternatively, the body 10 can have an operative distal end 12 remote from the proximal end 14 and/or the handle or grip disposed thereon, or can be configured for insertion through a cannula, portal, or opening in the skin, which can be advantageous in arthroscopic and percutaneous applications. The body 10 of the device 1 can also be appropriately sized and possibly adapted to mate with an arthroscope, laparoscope, endoscope, catheter or other instrument for surgical use inside the body 10. While the illustrated embodiment shows a body 10 as an integrated or unibody element, the device 1 can have separate or multiple bodies, such as one body for the delivery needle 16 and capture needle 18 suitable for insertion into the body (i.e., of a patient) and a separate or remote second body containing the injection device 26 and/or the needle driving elements adapted to be outside the body, with the two bodies in communication with one another to transfer, for example, the force of the needle driving elements, the adhesive material 32 to the needles, control or sensor signals, and so on. The distal end 12 of the body 10 can have one or more openings 37, 39 or cutouts formed therein to allow the delivery needle 16 and/or the capture needle 18 to extend therethrough. The shape, size, and spacing of the openings 37, 39 can vary widely, as one skilled in the art will recognize, and can be suited to the shape and spacing of the delivery needle 16 and capture needle 18, which will be discussed in more detail below.

The device 1 can have a delivery needle 16 adapted to carry a suture 38, as previously mentioned. The delivery needle 16 can have a variety of configurations, but in an exemplary embodiment the delivery needle 16 has a relatively straight elongate body 10 with a distal tip 34 configured to pierce bone. Alternatively, the delivery needle 16 can be curved, tapered or segmented and/or have a sharp, rounded, pointed, flat or other distal tip 34. The delivery needle 16 can have a cross-sectional shape that is circular, rectangular, square, or virtually any other shape. The delivery needle 16 can also be of virtually any length, although in some cases it can be advantageous for the delivery needle 16 to be of sufficient length to penetrate into cancellous bone, as will be discussed below. While a range of materials are suitable, typically the delivery needle 16 is formed of a bio-compatible material such as stainless steel or a titanium alloy to provide sufficient hardness or rigidity to pierce bone.

Figure 1B:
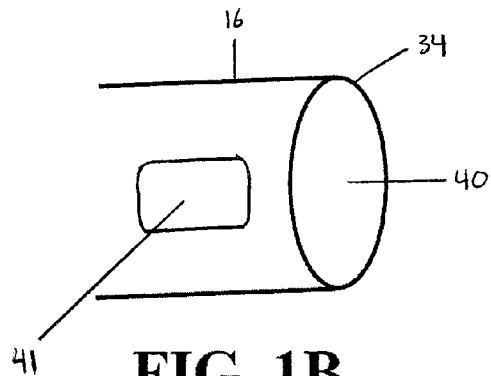
FIG. 1B is an enlarged view of a distal tip of a delivery needle of the device shown in FIG. 1A.
Figure 1C:
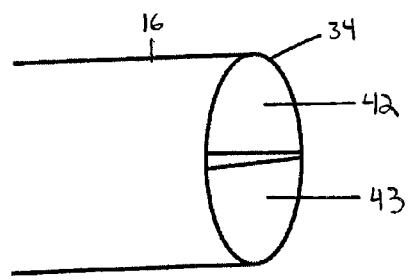
FIG. 1C is an enlarged view of an alternate distal tip of a delivery needle of the device shown in FIG. 1A.
Figure 1D:
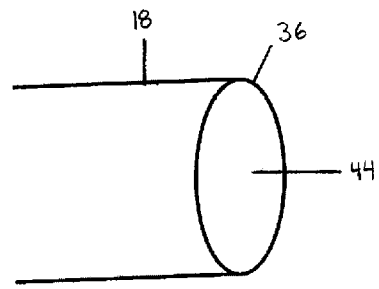
FIG. 1D is an enlarged view of a distal tip of a capture needle of the device shown in FIG. 1A.

The delivery needle 16 can include any of a variety of mechanisms to carry or engage suture 38. For example, the delivery needle 16 can include a suture engaging element such as a channel, groove, grasper, hook, loop, clasp, clamp, spur, or the like, disposed near or at a portion of the needle 16, such as the distal tip 34, to hold, engage or carry the suture 38 or a loop of suture 38 as the delivery needle 16 extends distally. The suture engaging element can be adapted to receive a suture 38 manually or to automatically engage the suture 38 as the delivery needle 16 advances distally. Alternatively, as shown in the illustrated embodiment of FIGS. 1B-1C, the delivery needle 16 has a lumen 40 formed therein and adapted for delivery of a suture 38 and optionally an adhesive material 32 to the distal tip 34 thereof or to a distal opening on the needle near the distal tip 34. The lumen 40 can run the length of the delivery needle 16 or it can also extend through a subsection thereof and form an opening 41 in the needle sidewall, for example to enable loading the suture 38 from the side of the needle. The suture 38 can be fed into the delivery needle 16 automatically, such as with a feed mechanism integrated into the device 1 itself, or manually, such as with a spool or plunger element. Additionally, the delivery needle 16 can have any number of lumens, for example, in another embodiment shown in FIG. 1C, the delivery needle 16 can include a first lumen 42 to carry a suture 38 and a second lumen 43 which can be in communication with the injection device 26 to pass an adhesive material 32 therethrough. If the delivery needle 16 has a single lumen 40, the injection device 26 can be in communication with the lumen 40 and as the result the adhesive material 32 can flow through the same lumen 40 as the suture 38.

The device 1 can also have a capture needle 18 adapted to receive the suture 38 carried by the delivery needle 16, as previously discussed. The capture needle 18 can have a variety of configurations, but in the illustrated embodiment the capture needle 18 has a relatively straight elongate body 10 with a bone piercing distal tip 36. Alternatively, the capture needle 18 can be curved, tapered or segmented and/or have a sharp, rounded, dull, pointed, flat or other distal tip 36. The capture needle 18 can have a cross-sectional shape that is circular, rectangular, square, or virtually any other shape. The capture needle 18 can also be of virtually any length, although in some cases it can be advantageous for the delivery needle 16 to be of sufficient length to penetrate into cancellous bone, as will be discussed below. While a range of materials are suitable, typically the capture needle 18 is formed of a bio-compatible material such as stainless steel or a titanium alloy to provide sufficient hardness or rigidity to pierce bone.

The capture needle 18 can be solid or optionally include one or more lumens 44 formed therein, such as any the lumen 40 or lumens 42, 43 described previously with respect to the delivery needle, to act as a vent, for example, to the adhesive material 32.

The capture needle 18 can be disposed at any distance from the delivery needle 16, although in the illustrated embodiment the capture needle 18 is disposed adjacent to the delivery needle 16. In other embodiments the delivery needle 16 and capture needle 18 can be spaced relatively closely, such as about 4 to 10 millimeters, for arthroscopic applications, for example, for passage through a surgical cannula to a repair site, and can be spaced relatively widely (e.g., about 4 to 20 millimeters for percutaneous applications. The spacing need not be fixed but can be user-customizable or adjustable. The capture needle 18 can also be arranged such that its path intersects the path of the delivery needle 16, i.e., when the delivery needle 16 and the capture needle 18 are distally advanced. The capture needle 18 and delivery needle 16 can be arranged such that their paths intersect in a number of ways, however, in the illustrated embodiment, the capture needle 18 extends from the body 10 of the device 1 from a position adjacent the delivery needle 16 and is oriented at an angle to the delivery needle 16 such that when advanced distally by the capture needle driving element 22, its path intersects the path of the delivery needle 16 when the delivery needle 16 is distally advanced. In this respect, the delivery needle 16 itself can be parallel to or angled with respect to the body 10 of the device 1. Alternatively, the capture needle 18 can be arranged parallel to the delivery needle 16. As previously mentioned, either or both of the delivery needle 16 and the capture needle 18 can be curved along at least part of their length, which can allow the path of the capture needle 18 to intersect the path of the delivery needle 16. The delivery needle 16 and the capture needle 18 can be arranged such that the intersection of the paths of the deployed delivery and capture needles occurs at a preset or known point distal to the device 1, or at a known depth in tissue or bone. The intersection point or intersection depth can also be user-customizable or user-adjustable.

In use, the capture needle 18 can receive or capture the suture 38 from the delivery needle 16 in many ways. For example, the capture needle 18 can advance to or through a suture-capture opening, e.g., a keyhole-shaped opening, formed in the distal tip 34 of the delivery needle 16 such as is described in U.S. Patent Application Publication No. 2005/0283170, which is hereby incorporated by reference in its entirety. The capture needle 18 can also have a moveable suture engaging element such as a suture grasper, a hook or wedge which can be actuated by a proximal to the capture needle 18. Alternatively the suture 38 can be deployed with the delivery needle 16 attached or tied to its own releasable tip or needle-point (i.e., a free tip) formed of a rigid material which can be ensnared or grabbed by the capture needle 18 at the intersection and withdrawn with the capture needle 18.

Figure 2:
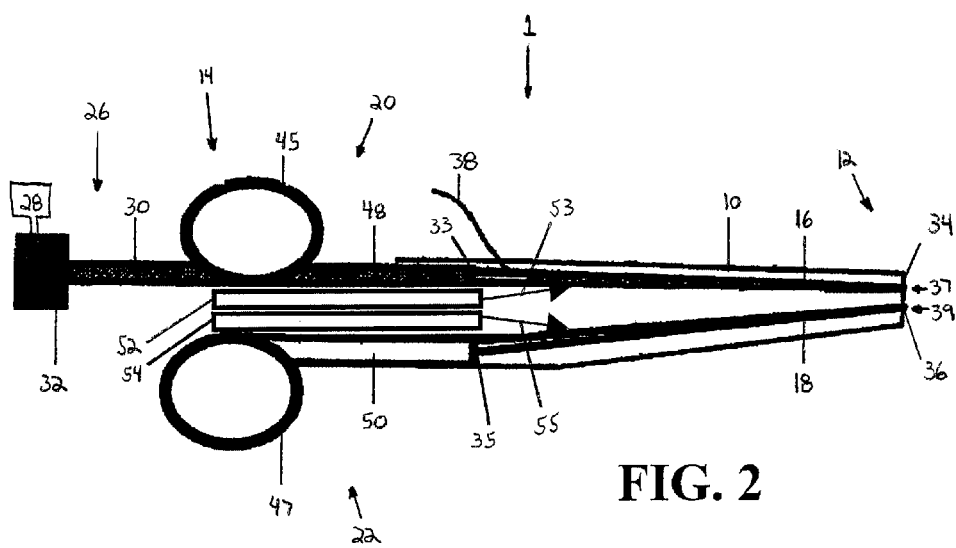
FIG. 2 illustrates an alternate embodiment of a bone suturing device having two ultrasonic driving elements.

As previously explained, the delivery needle 16 can be associated with a delivery needle driving element 20 for advancing the delivery needle 16 distally and the capture needle 18 can be associated with a capture needle driving element 22 for advancing the capture needle 18 distally. Thus the needle driving elements are adapted to advance the delivery needle 16 and/or capture needle 18 distally with sufficient force to penetrate soft tissue and underlying cortical bone. While the needle driving elements can have a variety of designs, in the illustrated embodiment the needle driving elements are shown as mechanical drivers with handles 45, 47 to allow the user to grip and/or control the driving element. The handles 45, 47 may be of virtually any shape but are shown as loop or ring-shaped. The handles 45, 47 can be attached to rods 48, 50 to deliver a distal force to the delivery needle 16 or capture needle 18, respectively. The mechanical drivers can be replaced or assisted by electric pumps or motors, geared mechanisms including worm gears and gear-reducers, screw mechanisms, air-pressure drivers, vibratory mechanisms, pneumatics, hydraulics, or any other mechanically leveraged mechanisms, as will be understood by one skilled in the art. The needle driving elements can also be or include one or more ultrasonic drivers 24. The ultrasonic driver 24 can have a wide variety of configurations, including any high-frequency or ultrasonic driver 24 capable of generating vibration, reciprocation, or force suitable for driving a delivery and/or capture needle 18 into a bone. For example, the ultrasonic driver 24 can be a piezoelectric driver or transducer providing a directed vibrational excitation to the distal tips 34, 36 of the needles. The piezoelectric driver may include a resonant free mass or a horn that may direct or amplify the waves generated by the ultrasonic driver 24. As shown in FIG. 1A, a single ultrasonic driver 24 may separately associated with or engage the delivery needle 16 and the capture needle 18 such as with a mechanical switch or detachable coupling. However, as depicted in FIG. 2, the device 1 optionally includes two ultrasonic drivers, a first ultrasonic driver 52 connected to the delivery needle 16 and a second ultrasonic driver 54 connected to the capture needle 18, eliminating the need to associate a single ultrasonic driver 24 to both needles. The ultrasonic driver 24 can also be arranged to direct ultrasonic vibration or energy into or against the adhesive material 32 in the lumen 40 of the delivery needle 16, for example via an association with the injection pump 30, the reservoir 28 of the injection device 26, or the lumen 40 of the delivery needle 16 itself. The ultrasonic driver 24 can thus provide an excitatory or motive force to the adhesive material 32 to cause or to assist a flow of adhesive material 32 through the delivery needle 16. Such an alternative configuration may allow the lumen 40 of the delivery needle 16 to be a smaller size than otherwise might be the case. The ultrasonic device can also be coupled to the suture 38 or the lumen 40 of the delivery needle 16 to provide an excitatory or motive force to the suture 38.

As previously mentioned, the device 1 can include an injection device 26 arranged at the proximal end 33 of the delivery needle 16 to deliver an adhesive material 32 therethrough. While the injection device 26 can have a variety of configurations, in the illustrated embodiment it has a reservoir 28 to store the adhesive material 32 and an injection pump 30 to move the adhesive material 32 from the reservoir 28 through the delivery needle 16. The reservoir 28 can have virtually any size and shape and can be a bladder, tank, removable cartridge, or any other storing element for storing, holding, mixing or agitating the adhesive material 32. The reservoir 28 can have any number of subsidiary bladders or compartments for holding adhesive compounds having multiple components or ingredients that must be stored separately, and can also have an agitation or mixing element, which in some cases can be the ultrasonic driver 24, disposed therein. The reservoir 28 can also include a heating element to bring an adhesive material 32 to a desired or appropriate temperature for delivery. The injection pump 30 may include any pumping mechanism including an electric pump, driving piston, impeller, pneumatic or hydraulic system, screw mechanism, and so on. The injection pump 30 may be in communication with the delivery needle 16 or the lumen 40 formed therein in a variety of ways, such as by a tube, coupling, hollow shaft, channel or tunnel formed in the body 10, or any passageway allowing adhesive material 32 to flow therethrough. In addition, the injection pump 30 can be in communication with a separate and distinct delivery tube or shaft associated with the delivery needle 16 to deliver the adhesive material 32 to the distal tip 34 of the delivery needle 16.

One skilled in the art will appreciate that the bone suturing device as previously described can have a variety of other configurations. For example, the capture needle 18 can have one or more lumens 44 formed therein and the injection device 26 can be connected thereto to deliver an adhesive material 32 through one or more of the lumens 44. The delivery needle 16 can have a lumen 40 to act as a vent. The addition of other delivery needles or capture needles or needle driving elements is also contemplated and within the scope of this disclosure, as is the omission of components such as the injection device 26 or ultrasonic driver(s) 24.

Figure 3A:
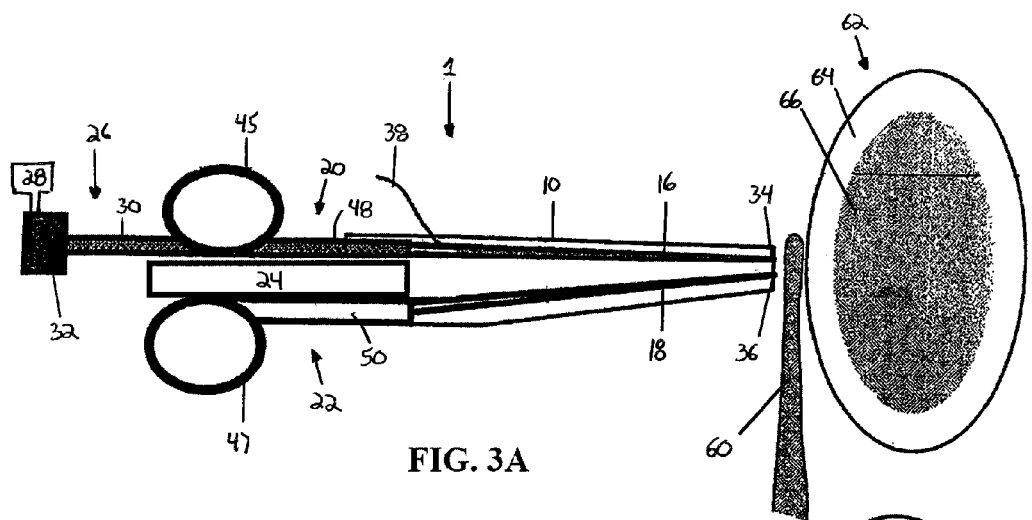
FIG. 3A illustrates the device shown in FIG. 1A positioned for use in a procedure for suturing soft tissue to bone.
Figure 3B:
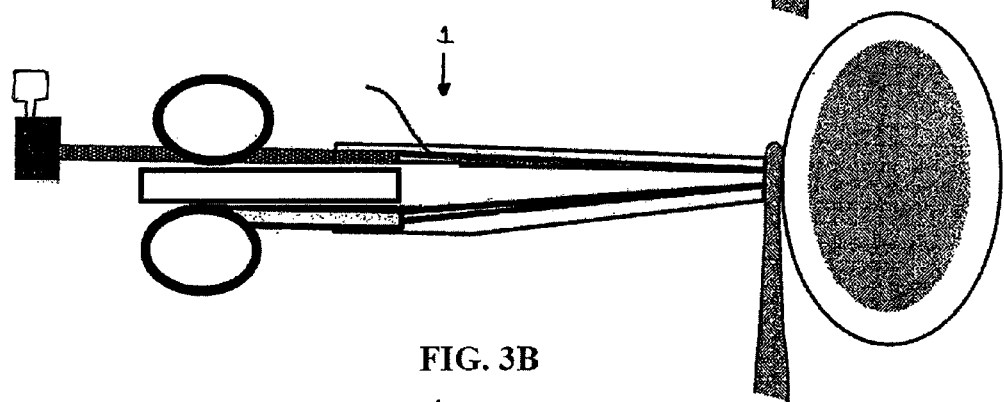
FIG. 3B illustrates the device shown in FIG. 1A positioned against soft tissue in the procedure for suturing soft tissue to bone.

The present invention also provides methods for suturing soft tissue to bone. In an exemplary embodiment, the methods allow a suture to be placed through soft tissue and into bone and reinforced with an adhesive material. In one exemplary method, a bone suturing device such as device 1 can be placed against soft tissue 60 over bone 62, as illustrated by FIGS. 3A-3B. The soft tissue 60 can be any kind of soft tissue, such as a tendon, ligament, cartilaginous tissue, or the like, and have virtually any thickness. The bone 62 can be any bone in any condition including healthy, damaged, osteoporotic bone. In the illustrated embodiment, the soft tissue 60 is initially in a condition in which it is detached from the underlying bone 62, which includes outer cortical bone 64 and inner cancellous bone 66. In many cases it is advantageous to place the stitch of suture 38 in the cancellous bone 66 so the suture 38 can pass behind the relatively dense cortical bone 64, as will be discussed in more detail below. The device 1 can be positioned at the surgical site in a variety of ways. In the illustrated embodiment, the device 1 is positioned against the soft tissue 60 which is placed against the bone 62. In other embodiments, the bone 62 can be exposed and the device 1 positioned against the bone 62 for placing a suture 38 therein, the soft tissue 60 optionally being sutured to the bone 62 in a separate step or procedure.

The device 1 can be loaded with suture 38 in any number of ways. As shown in FIGS. 3A-3B, the suture 38 is placed into the lumen 40 of the delivery needle 16 and advanced to the distal tip 34 of the delivery needle 16. Alternatively, the suture 38 can be engaged in a suture engaging element such as a groove, grasper, or hook on the delivery needle 16, or the suture 38 can also be loaded using an automatic feeding mechanism of the device 1. The suture 38 can be virtually any type of suture suitable for surgical use, including bio-absorbable and non-absorbable sutures. In some cases it can be advantageous to use a relatively stiff, robust or braided suture so as to aid in advancing the suture through the delivery needle 16. The suture 38 can be loaded at any time, for example before or after the device 1 is positioned or before or after the delivery needle 16 is advanced into bone 62, as will be discussed below in more detail.

Figure 3C:
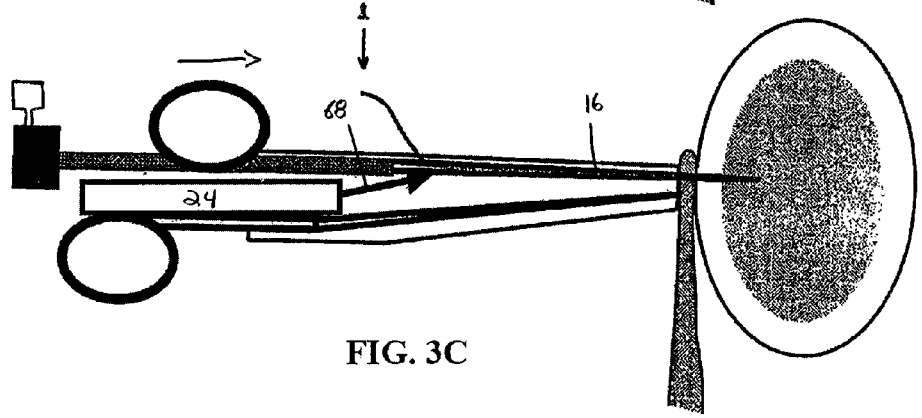
FIG. 3C illustrates the device shown in FIG. 1A with the delivery needle deployed into the bone in the procedure for suturing soft tissue to bone.

To place the suture 38, the delivery needle 16 can be advanced distally, which may be accomplished in a variety of ways. In the illustrated embodiment of FIG. 3C, the delivery needle 16 is advanced into bone 62 by actuating the handle 45 of the delivery needle driving element 20 and is effective to cause the sharp distal tip 34 of the delivery needle 16 to pierce the soft tissue 60 and cortical bone 64 and to reach the cancellous bone 66. In addition, in FIG. 3C an ultrasonic driver 24 is effective to provide an excitatory force to the delivery needle 16, as indicated by the arrow 68, to drive the delivery needle 16 distally with less mechanical force from the handle 45. Thus the handle 45 can be advanced to provide a guiding force instead of or in addition to a driving force. Any delivery needle driving element 20, as discussed previously, can be used or activated to advance the suture 38 distally or assist the advancement of the suture 38.

The capture needle 18 can be advanced distally in a variety of ways to capture the suture 38 from the delivery needle 16. In the illustrated embodiment of FIG. 3D, the capture needle 18 is advanced into bone 62 by actuating the handle 45 of the delivery needle driving element 20 and is effective to cause the sharp distal tip 34 of the delivery needle 16 to pierce the soft tissue 60 and cortical bone 64 and to reach the cancellous bone 66. In addition, as shown, an ultrasonic driver 24 is effective to provide an excitatory force to the capture needle 18, as indicated by the arrow 68, to drive the delivery needle 16 distally with less mechanical force from the handle 45. The capture needle 18 can be advanced such that its path intersects or nearly intersects the path of the delivery needle 16 in the cancellous bone 66. For example, in the illustrated embodiment the capture needle 18 is advanced at an angle relative to the delivery needle 16. The capture needle 18 can also be advanced parallel to the delivery needle 16 or in stages, e.g., a straight portion of the capture needle 18 can be advanced, then a flexible curved portion of the capture needle 18 can be advanced through a lumen 44 formed in the straight portion of the capture needle 18, and so on. In some cases the capture needle 18 can be advanced to meet the delivery needle 16 outside the cancellous bone 66. For example, the needles can meet in the cortical bone 64 or in soft tissue 60. However, it can be advantageous to advance to the capture needle 18 to meet the delivery needle 16 in the cancellous bone 66 because the cancellous bone 66 can be less dense than other bone, which can aid in passing suture 38.

Figure 3D:
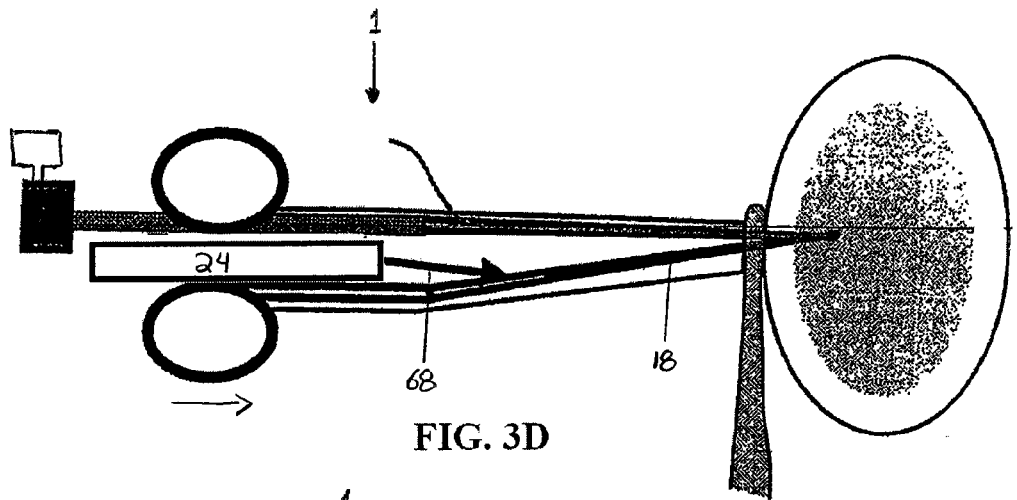
FIG. 3D illustrates the device shown in FIG. 1A with the capture needle deployed into the bone in the procedure for suturing soft tissue to bone.
Figure 3E:
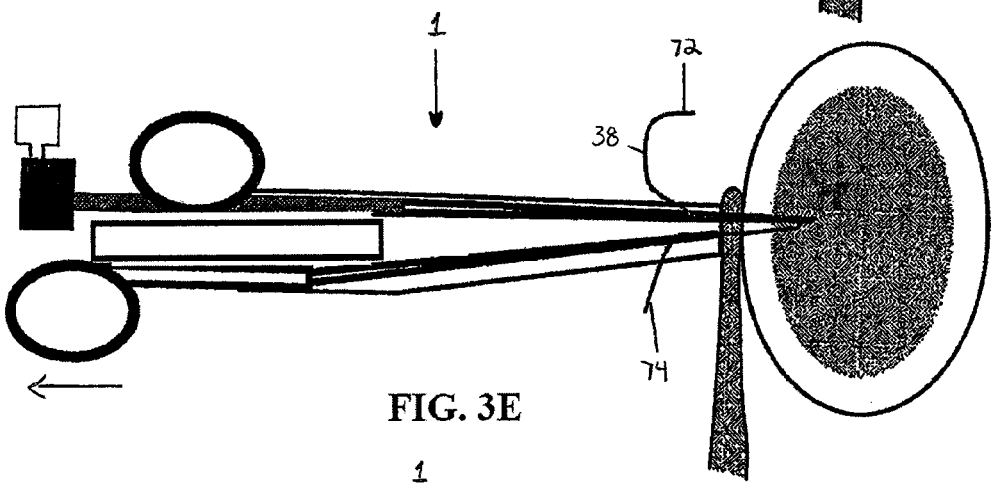
FIG. 3E illustrates the device shown in FIG. 1A with a suture passed between the delivery needle and the capture needle in the procedure for suturing soft tissue to bone.

Suture 38 can be passed from the delivery needle 16 to the capture needle 18 using a wide array of techniques. As shown in FIGS. 3D-3E, the handle 47 of the capture needle 18 can be actuated to withdraw the capture needle 18 to cause the tip of the capture needle 18 to engage or receive the suture 38, as previously described. Alternatively, a suture-passing control can be actuated to cause a moveable suture engaging element or suture grasper to engage the suture held by the delivery needle 16. The suture 38 can also be manually passed from the delivery needle 16 to the capture needle 18, e.g., through the lumen 40 of the delivery needle 16 and/or the capture needle 18 or from another access opening or hole formed in the bone 62. The capture needle 18 can also be withdrawn without capturing the suture 38 and a tool inserted into the hole formed by the capture needle 18 to retrieve the suture 38. In use, if the capture needle 18 receives the suture 38 the capture needle 18 can be withdrawn to pull the suture 38 and exit the bone 62 and the soft tissue 60, as shown in FIG. 3E. In some cases, however, it can be advantageous to omit passing of the suture 38 altogether and leave the suture 38 in the cancellous bone 66.

Figure 3F:
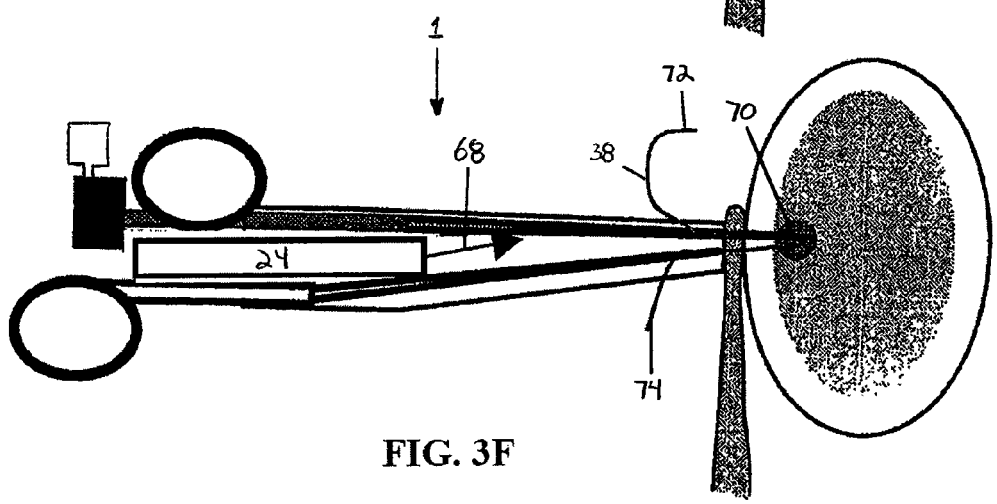
FIG. 3F illustrates the device shown in FIG. 1A with an adhesive material delivered into the bone in the procedure for suturing soft tissue to bone.

An adhesive material 32 can optionally be delivered into the bone 62. In FIG. 3F, an injection device 26 is effective to cause an adhesive material 32 to flow into the cancellous bone 66 via an injection pump 30 activated to pump the adhesive material 32 from the reservoir 28 into the bone 62. Alternatively, a manual pump can be operated, a screw mechanism can be turned, a plunger depressed, or the like, to deliver the adhesive material 32 into the bone 62. The adhesive material 32 can be delivered to the bone 62 through the distal tip 34 of the delivery needle 16 through the lumen 40 formed in the delivery needle 16, through the distal tip 36 of the capture needle 18 via a lumen 44 formed in the capture needle 18, or through the distal tips 34, 36 of both the delivery needle 16 and the capture needle 18. The ultrasonic driver 24 can also be engaged to deliver or assist in delivering the adhesive material 32 to the bone 62. The adhesive material 32 can form a plug or bolus 70 in the opening formed by the delivery needle 16 and the capture needle 18 and in the bone 62, as shown in FIG. 3F.

Various kinds of adhesive materials 32 can be employed with the device 1. The adhesive material 32 can be any substance or compound suitable for surgical use with bone, such as a bone cement, resin, polymer capable of drying, curing, or polymerizing to adhere to the suture 38 and/or to adjacent bone 62. In an exemplary embodiment, the adhesive material 32 can be a polymethylmethacrylate. In other embodiments, the adhesive material 32 can be a bone cement such as a calcium phosphate or calcium sulfate bone cement. The adhesive material 32 can be light-activated and preferably can be adapted to flow through the lumen of a needle, for example, as it is pumped or injected through the lumen 40 of the delivery needle 16 by an injection device 26 and/or ultrasonic driver 24. The adhesive material 32 can also be a polyurethane, which in some cases can be at least partially derived biologically derived. Suitable polyurethanes are described, for example, in U.S. Pat. Nos. 6,306,177, 6,140,452, and 4,743,632, each of which is hereby incorporated by reference in its entirety.

The adhesive material 32 can be vented, which can be performed in any number of ways. In the illustrated embodiment, the capture needle 18 is used to vent the adhesive material 32 with a lumen 44 formed therein. The venting can occur any point, for example, before or after withdrawal of the capture needle 18. If the capture needle 18 is first withdrawn, the capture needle 18 can be reinserted into the bone 62 to vent the adhesive material 32. In some cases, the lumen 40 formed in the delivery needle 16 can be used as a vent.

Figure 3G:
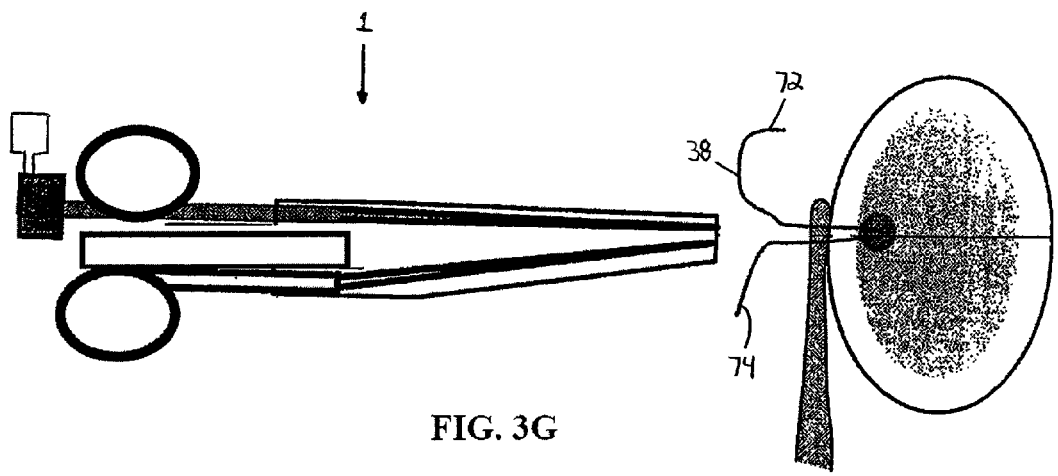
FIG. 3G illustrates the device shown in FIG. 1A removed from the soft tissue following the procedure for suturing soft tissue to bone.

As one skilled in the art will understand, the delivery needle 16 and/or the capture needle 18 can be withdrawn by actuating the handle 47. The device 1 can be removed from the soft tissue 60 to leave two suture ends 72, 74 of the suture 38 exposed. The suture ends 72, 74 of the suture 38 can be secured above the bone 62 and/or soft tissue 60 using known techniques. For example, the suture ends 72, 74 of the suture 38 can be tied into a knot, a fastener or locking device can be applied, adhesive material 32 can be delivered, and so on. Thus, in the illustrated embodiment of FIG. 3G, the method can result in a stitch of suture 38 placed through soft tissue 60 and into bone 62 with high resistance to pullout, a minimal footprint, and no foreign objects other than the suture 38 and adhesive material 32. Any or all of the foregoing steps can be repeated to effect single row, dual row, and/or mattress stitching techniques.

Figure 4A:
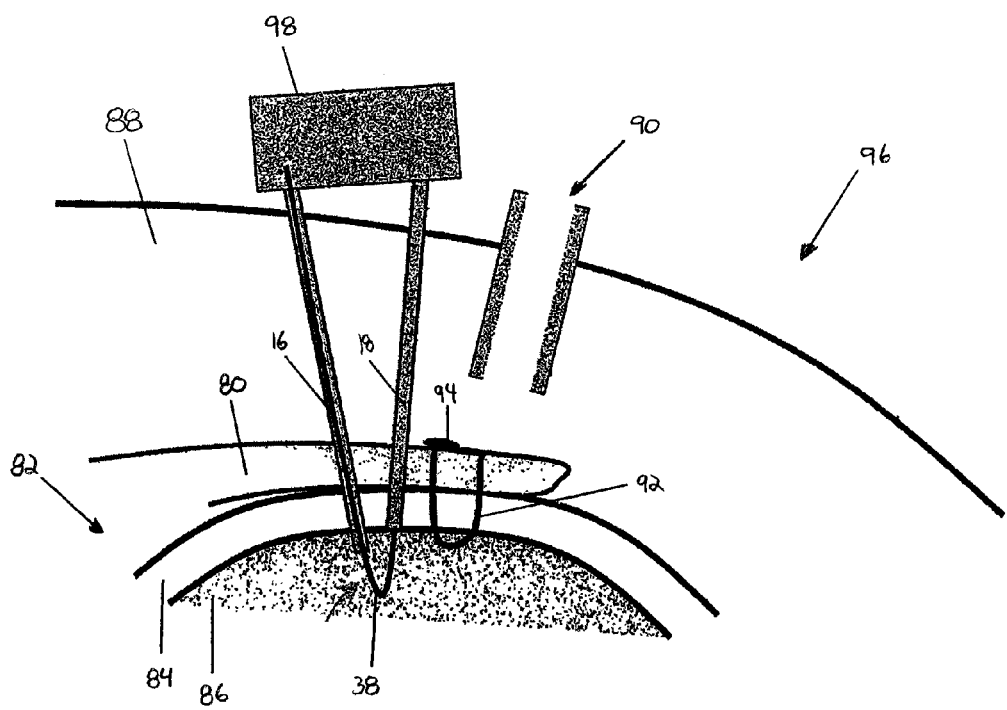
FIG. 4A schematically illustrates another embodiment of a bone suturing device shown in use during a percutaneous bone suturing procedure.

In another exemplary method, soft tissue can be sutured to the bone percutaneously. Percutaneous suturing can be performed in a wide variety of ways, however in the illustrated embodiment shown in FIG. 4A, an integrally housed suturing device 98 can be placed at a surgical site, such as the shoulder 96, and adjacent to skin 88 in order to suture soft tissue 80, such as a rotator cuff tendon, to bone 82, such as the humerus. In FIG. 4A, a suture 92 is shown already in place with one or more securing elements 94 such as a knot or fastener on the outside of the soft tissue 80. The bone 82 is seen to include cortical bone 84 and cancellous bone 86.

A portal 90, such as a cannula, tube, sleeve, or the like, can be formed in the skin 88 for visualization of the surgical site and/or suture manipulation, knot-tying, or virtually any other purpose. The portal 90 can also be used as a passageway for the delivery needle 16 and the capture needle 18 of the suturing device 98, in which case the lateral spacing between the delivery needle 16 and capture needle 18 can accommodate the width of the portal 90.

The delivery needle 16 and capture needle 18 can be advanced through the skin 88, through the soft tissue 80 and into bone 82 as previously described. In some cases, penetration through the skin 88 can be accomplished solely by manual force on the handles 45, 47, and penetration through the soft tissue 80 and/or bone 82 can be performed with the ultrasonic driver 24 or other needle driving element. Suture 38 can be passed from the delivery needle 16 to the capture needle 18, as previously described. In FIG. 4A, the suture 38 has been passed in the cancellous bone 86 and the capture needle 18 has been partially withdrawn. An adhesive material 32 can also be injected through the delivery needle 16, as previously described.

Figure 4B:
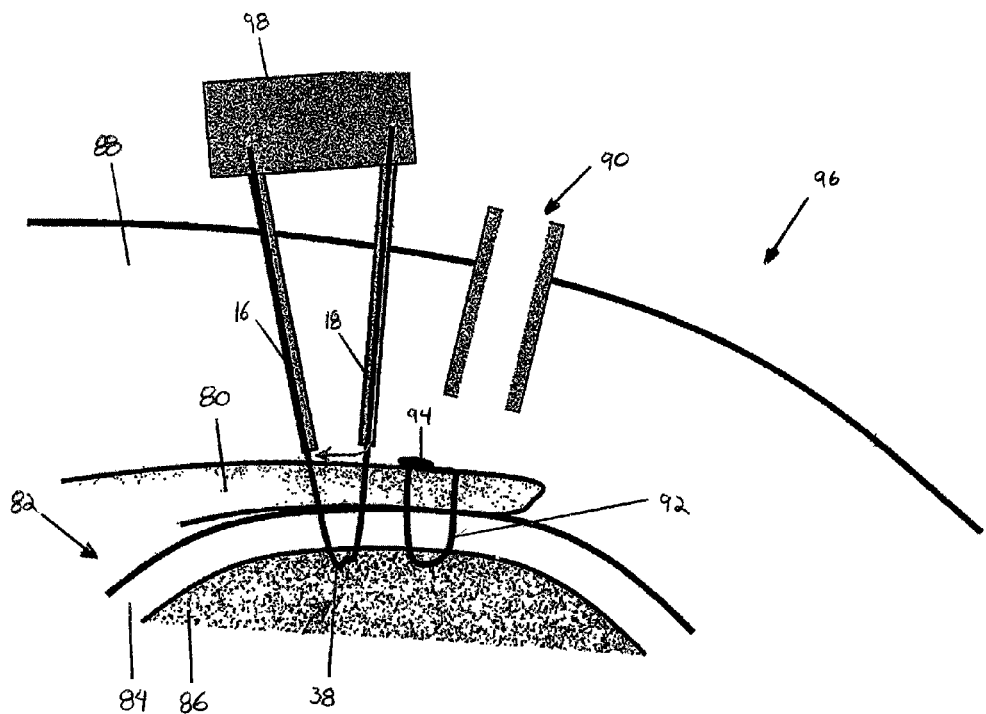
FIG. 4B illustrates the device shown in FIG. 4A withdrawn from the bone following a percutaneous bone suturing procedure.

The delivery needle 16 and the capture needle 18 can be withdrawn such that their distal tips 34, 36 are located above the soft tissue 80, as shown in FIG. 4B. The suture 38 can be passed (i.e., possibly a second passing of suture 38) from the capture needle 18 to the delivery needle 16, which can occur in a variety of ways, as previously described. Alternatively, the suture 38 can be passed manually, e.g., with tools manipulated through the portal 90. The suture 38 can also be passed by releasing the suture 38 from capture needle 18 and manipulating a suture engaging element on the delivery needle 16 to grab or engage the suture 38.

Figure 4C:
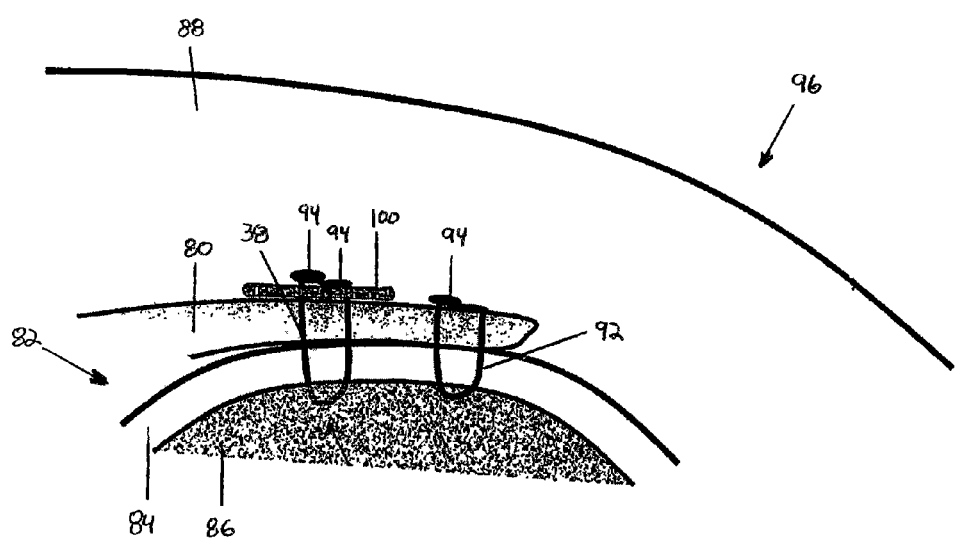
FIG. 4C illustrates two sutures placed in bone following the percutaneous bone suturing procedure illustrated in FIGS. 4A and 4B.

The suture 38 can be secured above the bone 82 using known techniques, as previously discussed. In FIG. 4B a securing element 94 has been employed with the suture 38. The securing element 94 can be a knot, a knotless device, fastener, or the like. The suture 38 can also be reinforced in any of a variety of ways. As shown in FIG. 4C, for example, one or more reinforcing elements 100 such as a bio-compatible plate, cover, patch, adhesive bolus, or buttress can be applied to the suture 38 or the securing element 94. Each of the securing element and reinforcing element can be placed in any known manner, such as by manipulating tools and materials through the portal 90.

As will be understood by those skilled in the art, the delivery needle 16 and capture needle 18 can be withdrawn from the skin, as discussed previously. In FIG. 4C, the device 98 has been removed from the surgical site to leave two sutures 38, 92 attaching the soft tissue 80 to the bone 82. The device 98 can be placed against the skin to place another suture, or alternatively, additional sutures can be placed before withdrawing the device 98 from the skin, which can be advantageous in single row, dual row, or mattress stitching.

Such procedures and methods can be performed at anywhere in the body in a wide variety of applications, including rotator cuff applications, meniscal repair, tendon or ligament repair, and so on, as will be understood by those skilled in the art. It should also be understood that the illustrations and description of use of the devices 1, 98 herein is by way of illustration only and a wide range of variations will be apparent to those skilled in the art, including variations on the content of the steps or procedures, the order of any steps performed, and the omission or addition of steps or procedures.

The devices disclosed herein and any components thereof can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning and/or replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. It is preferred that the device is sterilized. This can be done by any number of ways known to those skilled in the art including beta or gamma radiation, ethylene oxide, or steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for suturing soft tissue to bone, comprising:
    driving a delivery needle into bone, the delivery needle adapted to deliver a suture to bone;
    driving a capture needle into bone, without first pre-drilling a hole in the bone for the needle, such that a path of the capture needle intersects a path of the delivery needle;
    passing the suture from the delivery needle to the capture needle to withdraw the suture through the path of the capture needle; and
    securing the soft tissue to the bone with the suture.

2. The method of claim 1, wherein the method is conducted percutaneously.

3. The method of claim 1, wherein the steps of driving the delivery needle and the capture needle involve piercing the soft tissue.

4. The method of claim 1, further comprising the step of inserting a cannula into the skin and inserting the delivery needle and the capture needle through the cannula.

5. The method of claim 1, wherein the steps of driving the delivery needle and the capture needle are performed at least in part ultrasonically.

6. The method of claim 1, wherein the paths of the delivery needle and the capture needle intersect in cancellous bone.

7. The method of claim 1, wherein the step of securing the soft tissue to bone involves securing free ends of the suture outside the bone with at least one of a knot and a fastener.

8. The method of claim 1, wherein the suture is delivered to the bone simultaneously with the step of driving the delivery needle into the bone.

9. The method of claim 1, wherein the suture is delivered to the bone after the step of driving the delivery needle into the bone.

10. The method of claim 1, wherein the step of securing the soft tissue to the bone involves placing the soft tissue on the bone and driving the delivery needle and the capture needle through the soft tissue to be sutured.

11. The method of claim 1 and further comprising the step of delivering an adhesive material to an intersection of the paths of the delivery needle and the capture needle.

* * * * *